(12) United States Patent
Dietrich et al.

(10) Patent No.: US 12,354,457 B2
(45) Date of Patent: Jul. 8, 2025

(54) SURGICAL DEVICE SYSTEM, METHOD OF OPERATING THE SAME, AND WIRELESS LICENSE TAG

(71) Applicant: OLYMPUS WINTER & IBE GMBH, Hamburg (DE)

(72) Inventors: Stefan Dietrich, Potsdam (DE); Felix Köhnecke, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 146 days.

(21) Appl. No.: 18/122,464

(22) Filed: Mar. 16, 2023

(65) Prior Publication Data
US 2023/0306836 A1    Sep. 28, 2023

Related U.S. Application Data

(60) Provisional application No. 63/324,228, filed on Mar. 28, 2022.

(51) Int. Cl.
*G08B 21/18*    (2006.01)
*A61B 90/98*    (2016.01)
(Continued)

(52) U.S. Cl.
CPC .............. *G08B 21/18* (2013.01); *A61B 90/98* (2016.02); *G16H 40/40* (2018.01); *H04L 67/34* (2013.01); *H04W 76/15* (2018.02)

(58) Field of Classification Search
None
See application file for complete search history.

(56) References Cited

U.S. PATENT DOCUMENTS

2007/0244825 A1* 10/2007 Semmer ................ G06F 21/123
705/59
2008/0081354 A1*  4/2008 Qu ..................... A61K 48/0058
435/325
(Continued)

FOREIGN PATENT DOCUMENTS

EP          3066998 A1    9/2016
JP       2021-89748 A    6/2021
(Continued)

OTHER PUBLICATIONS

Apr. 2, 2024 Office Action Issued in Japanese Patent Application No. 2023-033401.
(Continued)

*Primary Examiner* — Thomas S McCormack
(74) *Attorney, Agent, or Firm* — Oliff PLC

(57) ABSTRACT

A surgical device system, and methods for operating a surgical device system, includes: at least one surgical instrument, a surgical generator for providing surgical energy to at least one surgical instrument, and at least one supplementary device for providing a supplementary function to at least one of the surgical generator and/or the at least one surgical instrument; the surgical generator being configured to wirelessly communicate with the at least one supplementary device, wherein the surgical generator and the at least one supplementary device are configured to establish a first communication channel for exchanging operational data, the first communication being defined by a number of first communication channel parameters; and wherein the surgical generator the at least one supplementary device are configured to establish a second communication channel for exchanging first communication channel parameters.

18 Claims, 7 Drawing Sheets

(51) Int. Cl.
*G16H 40/40* (2018.01)
*H04L 67/00* (2022.01)
*H04W 76/15* (2018.01)

(56) References Cited

U.S. PATENT DOCUMENTS

| | | | |
|---|---|---|---|
| 2014/0099888 A1* | 4/2014 | Flanagan | ................ H04W 4/80 |
| | | | 455/41.1 |
| 2016/0235374 A1* | 8/2016 | Miller | .................. A61B 5/0075 |
| 2018/0317826 A1 | 11/2018 | Muhsin et al. | |
| 2020/0076691 A1 | 3/2020 | O'Gwynn | |
| 2020/0405409 A1* | 12/2020 | Shelton, IV | ........... A61B 90/37 |

FOREIGN PATENT DOCUMENTS

| | | |
|---|---|---|
| JP | 2021-516113 A | 7/2021 |
| WO | 2019/173574 A1 | 9/2019 |
| WO | 2020/261071 A1 | 12/2020 |

OTHER PUBLICATIONS

Aug. 25, 2023 Extended Search Report issued in European Patent Application No. 23162000.6.
Dec. 14, 2022 Office Action issued in German Patent Application No. 10 2022 107 415.3.

* cited by examiner

SURGICAL DEVICE SYSTEM, METHOD OF OPERATING THE SAME, AND WIRELESS LICENSE TAG

FIELD OF THE INVENTION

The present disclosure is related to medical device systems. More specifically, the disclosure is related to the communication between accessories or components of medical device systems.

BACKGROUND

The way surgery is performed has evolved over time. While in classical surgery, stand-alone mechanical instruments like scalpels, forceps, scissors, and the like have been used for various invasive and non-invasive procedures, the mechanical function of those instruments has been replaced or supplement by energy functions like monopolar or bipolar electrosurgery, ultrasound surgery, microwave surgery, and the like. Surgical generators have been developed for providing surgical energy, usually in the form of electrical current, to respective instruments.

In addition to surgical generators, further supplementary devices have been developed for supporting the operation of surgical generators and instruments. Such supplementary devices include, but are not limited to, foot switches, irrigation pumps, suction pumps, coolant pumps, and the like.

In a common setup, one or more surgical generators, one or more surgical instruments, and one or more supplementary devices form a surgical system for coordinated provision of surgical and supplementary functions.

For the necessary communication of operational data between the components of a surgical system, the components are often connected via cabling. However, such cabling has significant drawbacks in related to operability and manoeuvrability in the operation theatre. To overcome these drawbacks, wireless communication has been employed in some instances.

Safe and secure wireless communication of operational data between components of surgical systems requires use of coded communication channels. In some surgical device systems, this has been achieved by providing a supplementary device for use with a surgical system together with a wireless communication interface, which can be connected to a surgical generator through a standard wired interface like a USB interface, an RS-232 interface, or a proprietary wired interface. Communication channel parameters of the wireless communication channel used by the respective supplementary device are pre-programmed in the supplementary device and the wireless communication interface. Examples of such supplementary devices are surgical foot switches WA91320W and WA94934W, available from Olympus Europa SE & Co. KG, Germany. It is one object of the present disclosure to provide a surgical system with improved flexibility.

Some medical devices are configured to provide a plurality of functionalities, whereas some functionalities may be subject to a separate license from the provider of the medical device. For activating such functionalities, a user may be required to enter a license key through a user interface of the medical device.

It is a further object of the present disclosure to provide medical devices where registration of licenses is improved.

SUMMARY OF DISCLOSURE

The present disclosure provides a surgical device system, comprising: at least one surgical instrument, a surgical generator for providing surgical energy to at least one surgical instrument, and at least one supplementary device for providing a supplementary function to at least one of the surgical generator and/or the at least one surgical instrument; the surgical generator being configured to wirelessly communicate with the at least one supplementary device, wherein the surgical generator and the at least one supplementary device are configured to establish a first communication channel for exchanging operational data, the first communication being defined by a number of first communication channel parameters; and wherein the surgical generator and the at least one supplementary device are configured to establish a second communication channel for exchanging first communication channel parameters.

The second communication channel may be independent from the first communication channel. A range of the second communication channel may be shorter than a range of the first communication channel. A bandwidth of the second communication channel may be lower than a bandwidth of the first communication channel. The second communication channel may be a Near Field Communication "NFC" channel. The second communication channel may be a Radio Frequency Identification "RFID" channel.

The first communication channel may be an IEEE 802.11 "WIFI" communication channel. The first communication channel may be a "Bluetooth" communication channel. Herein, the term "Bluetooth" is meant to cover any available versions of the "Bluetooth" communication standard provided by the Bluetooth Special Interest Group. The first communication channel may be an IEEE802.15.4 or "ZigBee" communication channel.

The at least one supplementary device may further be configured to transmit device characterization data and/or device identification data through the second communication channel. The at least one supplementary device may include at least one of a foot switch, a smoke evacuator, an irrigation pump, a suction pump, and a coolant pump. The operational data include at least one of an activation signal, a deactivation signal, a target flow rate, a current flow rate, a target pressure, a current pressure, a target temperature, a current temperature, a battery status, a connection quality, and a heartbeat signal.

The surgical generator may further be configured to receive, through a network connection, software update data for one or more of the supplementary devices, and to communicate such software update data to the one or more supplementary devices.

The present disclosure further provides a surgical device system, comprising at least one surgical instrument; a surgical generator for providing surgical energy to at least one surgical instrument; and at least one supplementary device for providing a supplementary function to at least one of the surgical generator and/or the at least one surgical instrument; the surgical generator being configured to communicate with the at least one supplementary device; wherein the surgical generator and the at least one supplementary device are configured to establish a first, wire-bound communication channel for exchanging operational data; and wherein the surgical generator and the at least one supplementary device are configured to establish a second, wireless communication channel for exchanging supplementary data.

The present disclosure provides a surgical generator of a surgical device system according to the above disclosure.

The present disclosure provides a supplementary device of a surgical device system according to the above disclosure.

The present disclosure further provides a method of operating a surgical device system, with the steps: establishing a second communication channel between a surgical generator and a supplementary device, exchanging first communication channel parameters through the second communication channel, establishing a first communication channel between the surgical generator and the supplementary device, using the first communication channel parameters, and exchanging operational data between the surgical generator and the at least one supplementary device through the first communication channel.

A method according to the present disclosure may further comprise a step of transmitting device characterization data and/or device identification data of the at least one supplementary device through the second communication channel.

The present disclosure further provides a method of operating a surgical device system with the steps: receiving, through a user interface, input data identifying a surgical procedure to be performed; reading, from a memory, a list of supplementary devices required for the surgical procedure to be performed; establishing a second communication channel between the electrosurgical generator and one or more supplementary devices within the reach of the second communication channel; receiving, through the second communication channel, device identification data and/or device characterization data from supplementary devices within the range of the second communication channel; checking if all supplementary devices required for the procedure to be performed have provided device identification data or device characterization data in response to the interrogation signal; and, if the check has been successful, establishing one or more first communication channels between the surgical generator and the supplementary devices.

The method may further include a step of, if the check has not been successful, outputting, through the user interface, an error message identifying missing supplementary devices required for the procedure to be performed.

The present disclosure further provides a medical device, comprising a control unit and a function unit, wherein the medical device is configured to provide a plurality of medical functionalities through the function unit, at least one of the plurality of functionalities being subject to a license, wherein the medical device further comprises a wireless communication unit configured to establish a wireless communication channel with a wireless license tag, and to obtain a license key for the at least one functionality from the wireless license tag. The medical device may be configured to communicate, after establishing the wireless communication channel with the wireless license tag, medical device identification data through the wireless communication channel.

The present disclosure further provides a wireless license tag, the wireless license tag being configured to establish a wireless communication channel with a medical device, and to communicate a license key to the medical device, the license key being stored on a memory element of the wireless license tag. The wireless license tag may be configured to store the license key in a first state and a second state, the first state representing an unused license key, and the second state representing a used license key. The wireless license tag may be configured to change the state of the stored license key from the first state to the second state after communication of the license key to the medical device.

The wireless license tag may be configured to receive, after establishing the wireless communication channel with the medical device, medical device identification data through the wireless communication channel, and to store the medical device identification data together with the license key in the second state. The wireless license tag may be configured to, when the license key is stored in the second state, communicate the license key to the medical device only if the medical device identification data received from the medical device matches the medical device identification data stored with the license key.

Some examples of the present disclosure are described in the following at hand of illustrative drawings. The examples described are provided for better understanding, and are not supposed to limit the scope of the appended claims in any way.

BRIEF DESCRIPTION OF THE DRAWINGS

The drawings show.

DETAILED DESCRIPTION

Figure 1:
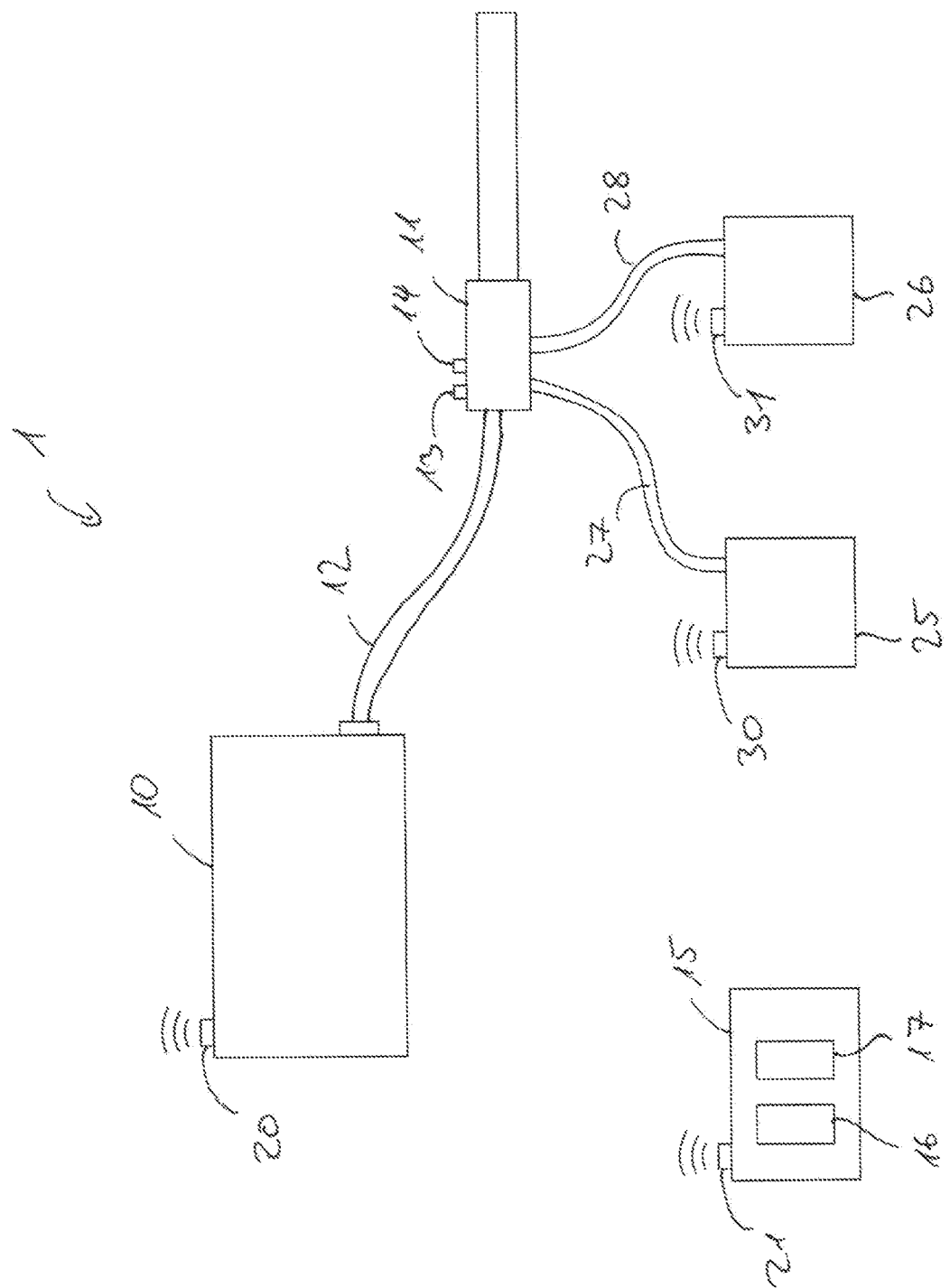
FIG. 1: A surgical device system.

FIG. 1 shows a surgical device system 1, including an electrosurgical generator 10 and an electrosurgical instrument 11. The electrosurgical instrument 11 is connected to the electrosurgical generator 10 through a cable 12 for transmitting electrosurgical therapy signals from the electrosurgical generator 10 to the electrosurgical instrument 11, and for exchanging configuration and/or operational data between the electrosurgical generator 10 and the electrosurgical instrument 11. The electrosurgical instrument 11 may comprise activation buttons 13, 14 on a grip portion of the electrosurgical instrument 11, so that they can be operated by a practitioner holding the electrosurgical instrument 11. Activation signals from the activation buttons 13, 14 may be communicated to the electrosurgical generator 10 through the cable 12.

The electrosurgical generator 10 may be any one of a radiofrequency generator, a microwave generator, an ultrasound generator, or a combination thereof. The electrosurgical instrument 11 may be any one of a cutting instrument, a sealing instrument, an ablation instrument, or a combination thereof. The surgical device system 1 further includes a wireless foot switch 15 with two pedals 16, 17. The wireless foot switch 15 may have more or less than two pedals, and may comprise additional control elements like toggle buttons, switches, or the like.

The electrosurgical generator 10 and the wireless footswitch 15 each include a wireless communication unit 20, 21. In the present example, the wireless communication units 20, 21 may be configured to communicate each other through electromagnetic signals using the IEEE 802.11 standard, commonly known as "WIFI". Therefore, the wireless communication units 20, 21 use a first wireless communication channel defined by a set of communication channel parameters including, but not limited to, a channel identification code, a channel authentication code, and the like. Alternatively, other electromagnetic communication standards, like "Bluetooth" or "ZigBee", may be used for the first wireless communication channel.

In the present example, the surgical device system includes further supplementary devices like an irrigation pump 25 and a suction pump 26, each connected to the surgical instrument 11 by tubes 27, 28. The irrigation pump 25 may be used to supply irrigation fluid to a surgical site through the tube 27 and the electrosurgical instrument 11. The irrigation fluid can be used to wash away debris or blood from the site. The suction pump 26 may be used to evacuate fluids like liquids, fumes, or gases from the surgical site, through the electrosurgical instrument 11 and the tube 28.

The irrigation pump 25 and the suction pump 26 also include wireless communication units 30, 31. The wireless communication units may also be configured to communicate with each other and/or with the one or more of the communication units 20, 21 through electromagnetic signals.

During operation of the surgical device system 1, a user may depress any of the activation buttons 13, 14 and/or the pedals 16, 17 of the wireless foot switch for activating different functions of the surgical device system 1.

The first pedal 16 may, when depressed, initiate issuing of a first electrosurgical therapy signal from the electrosurgical generator 10 to the electrosurgical instrument 11. The first electrosurgical signal may be a cutting signal, so that the electrosurgical instrument 11 can be used to cut through a tissue of interest. The second pedal may, when depressed, initiate issuing of a second electrosurgical therapy signal from the electrosurgical generator 10 to the electrosurgical instrument 11. The second electrosurgical signal may be a cauterization signal, so that the electrosurgical instrument 11 can be used to cauterize bleedings, like bleedings resulting from a previous tissue cutting operation. Depression of any one of the pedals 16, 17 of the wireless foot switch 15 is communicated to the electrosurgical generator 10 through the wireless communication units 21, 20.

The first activation button 13 on the electrosurgical instrument 11 may activate the irrigation pump 25. A practitioner may depress the activation button 13 e.g. if blood or debris accumulate in the surgical site, so that a liquid like sterile saline may be ejected from the electrosurgical instrument 11 to flush the blood or debris away. The second activation button 14 on the electrosurgical instrument 11 may activate the suction pump 26. A practitioner may depress the activation button 14 e.g. if fumes, blood, or irrigation liquid need to be evacuated from the surgical site. Activation signals of the activation buttons 13, 14 are communicated to the electrosurgical generator 10 through the cable 12, and are then communicated to the suction pump 25 and the irrigation pump 26 through the wireless communication units 20, 30, 31. For communication between the wireless communication units 20, 30, 31, the same communication channel may be used as for the communication between the wireless communication units 20 and 21.

For facilitating the communication between the devices of the surgical device system 1 as described above, the wireless communication units 20, 21, 30, 31 need to agree on communication channel parameters. In prior art systems, this has been achieved by providing each supplementary device with a dedicated pair of wireless communication units, one of which is fixed to the supplementary device, the other one is to be connected to the electrosurgical generator through a standard wired interface like a USB plug, or through a proprietary wired interface. However, such design tends to be bulky in case of multiple supplementary devices.

In a system according to the present disclosure, the wireless communication units 20, 21, 30, 31 agree on the communication channel parameters through a second wireless communication channel. The second wireless communication channel may be established between the wireless communication units 20, 21, 30, 31 using RFID or NFC technology. Therefore, the wireless communication unit 20 may include an RFID interrogator, and the wireless communication units 21, 30, 31 may include RFID transponders. The second communication channel is established by sending an interrogation signal through the RFID interrogator of the wireless communication unit 20, and by receiving the interrogation signal through the RFID transponders of the wireless communication units 21, 30, 31. The interrogation signal may include communication channel parameters for the first communication channel, which are pre-programmed in the wireless communication unit 20, and can then be applied by the wireless communication units 21, 30, 31. Alternatively, communication channel parameters may be negotiated between the wireless communication units 20, 21, 30, and 31.

An available communication range of the second wireless communication channel using RFID or NFC technology is much shorter than an available communication range of the first communication channel. Therefore, it may be necessary to move the supplementary devices 15, 25, 26 into the proximity of the electrosurgical generator 10 during setup of the surgical device system, so that the second communication channel can be established. This has the technical benefit that protection measures of the second communication channel against unauthorized access through other devices may not be necessary. For the first communication channel such protection measures can more easily be applied, as necessary parameters can previously be agreed by the participating devices through the second communication channel.

The second communication channel may also have a smaller communication bandwidth than the first communication channel. This does not present a problem because the volume of data to be communicated through the second communication channel is rather low, and will be in the range of only a few kilobyte.

After receiving the interrogation signal, the wireless communication units 21, 30, 31 may transmit response signals to be received by the wireless communication unit 20. The response signals may include identification and/or characterization information from the supplementary devices 15, 25, 26.

The electrosurgical generator 10 may use the identification and/or characterization information received from the supplementary devices 15, 25, 26 to verify that all supplementary devices required for an intended procedure are available. Therefore, a user may select a certain procedure from a list of available procedures through a user interface of the electrosurgical generator 10. The electrosurgical generator 10 may then read a list of requires supplementary devices from a memory, like an internal memory of the electrosurgical generator 10, or an external memory device connected to the electrosurgical generator 10.

If the electrosurgical generator 10 determines that all required supplementary devices are available, the electrosurgical generator 10 may proceed to establish the first wireless communication channel with the supplementary devices 15, 25, 26, so that the selected procedure may be performed. In case the electrosurgical generator 10 finds that one or more required supplementary devices have not sent a response signal to the interrogation signal, a respective error message may be output through a user interface of the electrosurgical generator 10.

During performance of the selected procedure, operational data is exchanged between the electrosurgical generator 10 and the supplementary devices 15, 25, 26. The operational data may include activation or deactivation signals sent from the wireless foot switch 15 to the electrosurgical generator 10, or from the electrosurgical generator 10 to the suction pump 25 or the irrigation pump 26. The operational data may further include target or current flow rates of the pumps 25, 26, target or current pressures of the pumps 25, 26, or the like. In other embodiments of a surgical device system not shown in the drawings, a coolant pump may be used as a supplementary device. In this case, the operational data may include target or current inflow and outflow temperatures of a coolant. I further embodiments of a surgical device system not shown in the drawings, a smoke evacuator may be used as a supplementary device. In this case, the operational data may include targe or current evacuation volume flows.

The operational data may further include battery status and/or connection quality data. The operational data may further include one or more heartbeat signals. Heartbeat signals can be used by the electrosurgical generator 10 and/or the supplementary devices 15, 25, 26 to determine if the first wireless communication channel is still available. In case of a loss of connectivity of the first wireless communication channel, the electrosurgical generator 10 and/or the supplementary devices 15, 25, 26 may be configured to take appropriate measures for maintaining patient safety.

In a further embodiment of a surgical device system, the electrosurgical generator may be configured to receive, through a network connection (not shown), software update data for one or more target supplementary devices of the supplementary devices 15, 25, 26. Such software update data may be received by the electrosurgical generator 10 at any time, and may be stored in a memory of the electrosurgical generator 10. After the first wireless communication channel has been established between the electrosurgical generator 10 and the one or more target supplementary devices, the electrosurgical generator 10 may communicate the software update data to the target supplementary devices, and the target supplementary devices may use the software update data for updating their internal operation software.

Figure 2:
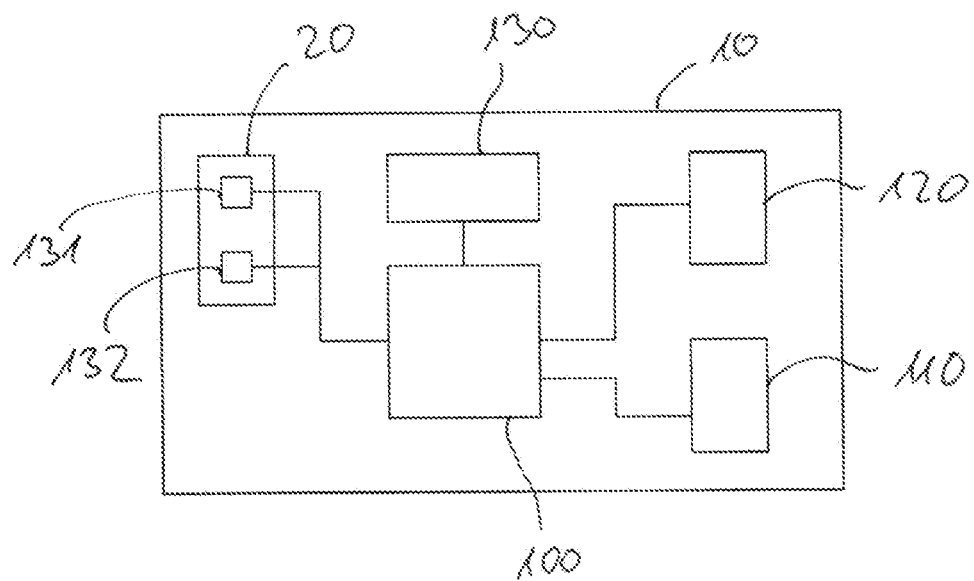
FIG. 2: an electrosurgical generator in a schematic view.

The internal design of the electrosurgical generator 10 is shown as a schematic view in FIG. 2. The electrosurgical generator 10 comprises a control unit 100 for controlling various functions of the electrosurgical generator 10. The control unit 100 may have a standard computer architecture involving one or more processors and one or more memory elements. Such standard computer architecture is known to the person skilled in the art and needs not be explained here in detail.

The electrosurgical generator 10 further comprises an electrosurgical function unit 110. The electrosurgical function unit may include a radiofrequency generator, an ultrasound generator, a microwave generator, or a combination thereof. The design of such electrosurgical function units in known from the art and needs not be explained here in detail.

The electrosurgical generator 10 further comprises a user interface 120. The user interface 120 may include one or more displays, control buttons, keyboards, a touch-sensitive displays, or combinations thereof. Through the user interface 120, the control unit may communicate operational and status information to a user, and receive input from a user. Input from a user may include, but is not limited to, selection of a procedure to be performed, selection of operational parameters for a selected procedure, or the like.

The electrosurgical generator further comprises a memory unit 130. The memory unit 130 may be part of the control unit 100, or may be separate therefrom. The memory unit 130 may be a Static Random Access Memory (S-RAM), a Dynamic Random Access Memory (D-RAM), a Read Only Memory (ROM), a Hard Disk Drive (HDD), a Solid State Disk (SSD), or a combination thereof. The memory unit 130 may store a list of electrosurgical procedures which can be performed with the electrosurgical generator 10. For each available procedure, the memory unit may store a list of supplementary devices required for the respective procedure.

The electrosurgical generator further comprises the wireless communication unit 20. The wireless communication unit 20 includes a WIFI antenna 131, an RFID interrogator 132, and associated circuitry (not shown).

The control unit 100 communicates with the electrosurgical function unit 110, the user interface 120, the memory unit 10, and the wireless communication unit 20 to operate as described above.

Figure 3:
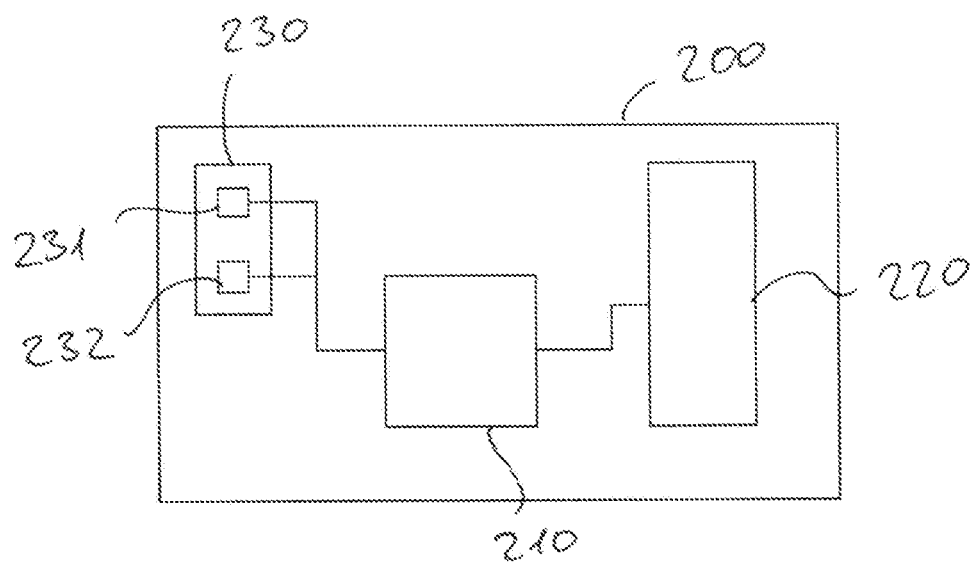
FIG. 3: a supplementary device in a schematic view.

FIG. 3 shows the internal design of a supplementary device 200 in a schematic view. The supplementary device 200 may be a foot switch similar to the foot switch 15, or a pump similar to the suction pump 25 or the irrigation pump 26, or another supplementary device. The supplementary device 200 comprises a supplementary device control unit 210 and a supplementary function unit 220. The supplementary device control unit 210 may have a standard computer architecture similar to the control unit 100 of the electrosurgical generator 10. The design of the supplementary function unit may vary widely depending on the type of supplementary function to be provided by the supplementary device 200.

If the supplementary device 200 is a foot switch like the foot switch 15, the supplementary function unit 220 may comprise one or more pedals, and one or more sensors for sensing whether the one or more pedals are depressed or not and, optionally, a force applied to the one or more pedals. If the supplementary device 200 is a pump like the suction pump 25, the irrigation pump 26, or a coolant pump, the supplementary function 200 may comprise a pump unit like a peristaltic pump, a piston pump, or the like, a drive unit for driving the pump unit, and one or more sensors for sensing one or more of a pressure of the pumped medium, a flow rate of the pumped medium, and a temperature of the pumped medium.

The supplementary device 200 further comprises a wireless communication unit 230, comprising a WIFI antenna 231 and an RFID transponder 232. The supplementary device control unit 210 communicates with the supplementary function unit 220 and the wireless communication unit 230 to operate as described above.

Figure 4:
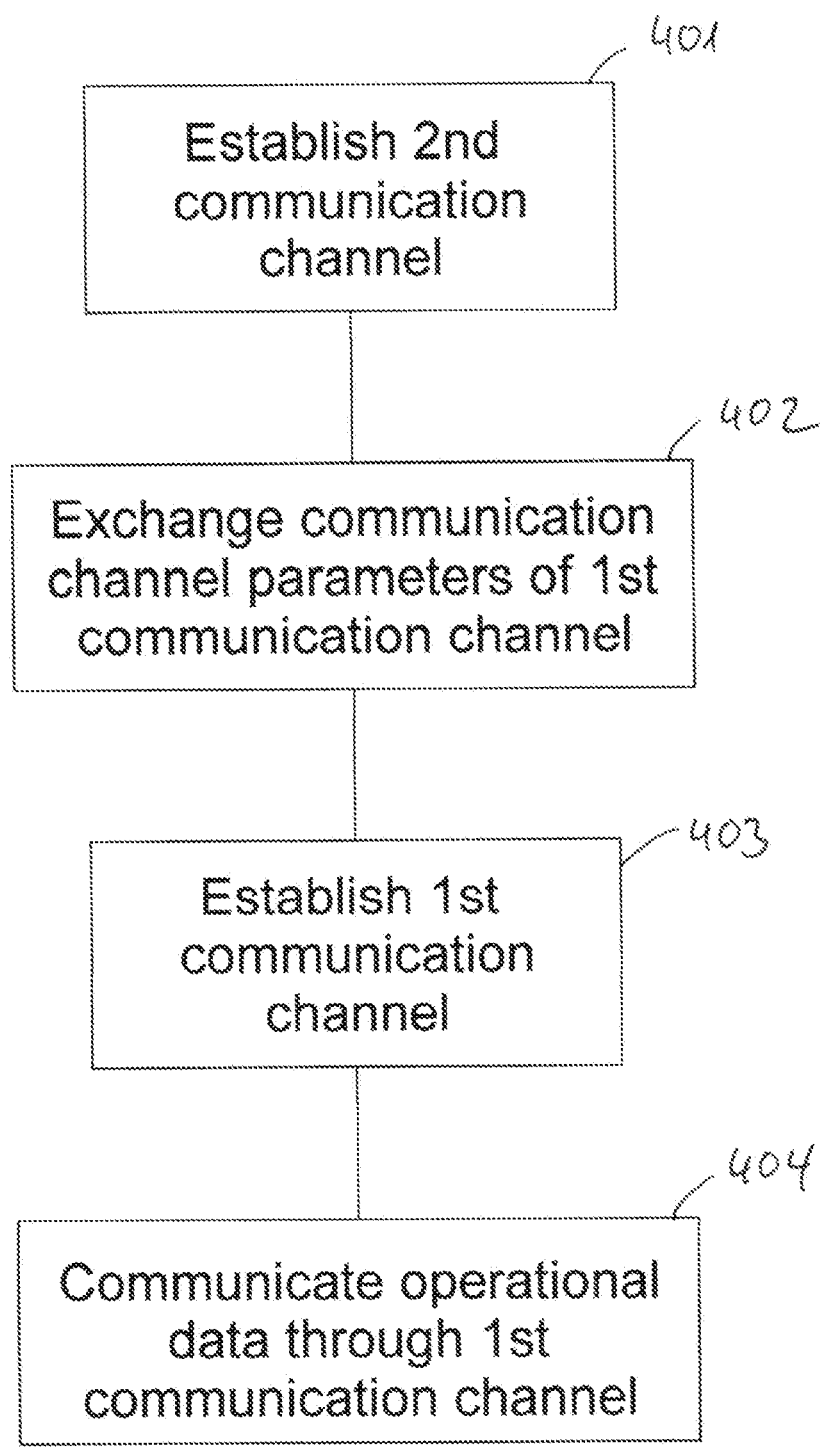
FIG. 4: a method of operating a surgical device system.

FIG. 4 shows a method of operating a surgical device system like the one described above. In a first step 401, a second communication channel is established between an electrosurgical generator and one or more supplementary devices.

For establishing the second communication channel, the electrosurgical generator may send an interrogation signal through a wireless communication unit. The interrogation signal may be an RFID interrogation signal. The interrogation signal may be received by supplementary devices within the range of the interrogation signal. After receiving the interrogation signal, any supplementary device may send a response signal, which may be received by the electrosurgical generator. Through this interrogation and response, the second communication channel is established between the electrosurgical generator and the one or more supplementary devices.

In a second step 402, the electrosurgical generator and the one or more supplementary devices exchange communication channel parameters of a first communication channel to be established between the electrosurgical generator and the one or ore supplementary devices. In some embodiments, the communication channel parameters include predetermined parameters stored in a memory of the electrosurgical generator. Such predetermined parameters may for example include a frequency band like 2.4 GHz, 4.9 Ghz, or the like, and a channel number like one of channels 1 to 14 in the 2.4 GHz band, of a WiFi connection. In some embodiments, the communication channel parameters may include dynamic parameters to be negotiated or agreed between the electrosurgical generator and the one or more supplementary devices. Such dynamic parameters may include encryption-related parameters, which may e.g. be determined by exchanging cryptographic keys between the electrosurgical generator and the one or more supplementary devices.

In a possible embodiment, the first and second step 401, 402 described above may be merged into a single step. In such embodiment, any necessary communication channel parameters may be included into the interrogation signal sent by the electrosurgical generator.

Together with the response signal, the one or more supplementary devices may transmit device characterization data and/or device identification data to the electrosurgical generator. The device characterization data and/or device identification data of the at least one supplementary device may be used by the electrosurgical generator to determine which kind of operational data is to be communicated with the at least one supplementary device through the first communication channel in a later step.

In a third step 403, a first communication channel is established between the electrosurgical generator and the one or more supplementary devices. Therefore, the respective devices may use the communication channel parameters agreed upon in the preceding steps to send and receive data through their respective wireless communication units.

In a fourth step 404, the electrosurgical generator and the one or more supplementary units communicate operational data through the first communication channel. The operational data may include activation or deactivation signals sent from a wireless foot switch to the electrosurgical generator, or from the electrosurgical generator to a suction pump or an irrigation pump. The operational data may further include target or current flow rates of pumps, target or current pressures of the pumps, or the like. The operational data may further include target or current inflow and outflow temperatures of a coolant to be provided through a coolant pump.

Figure 5:
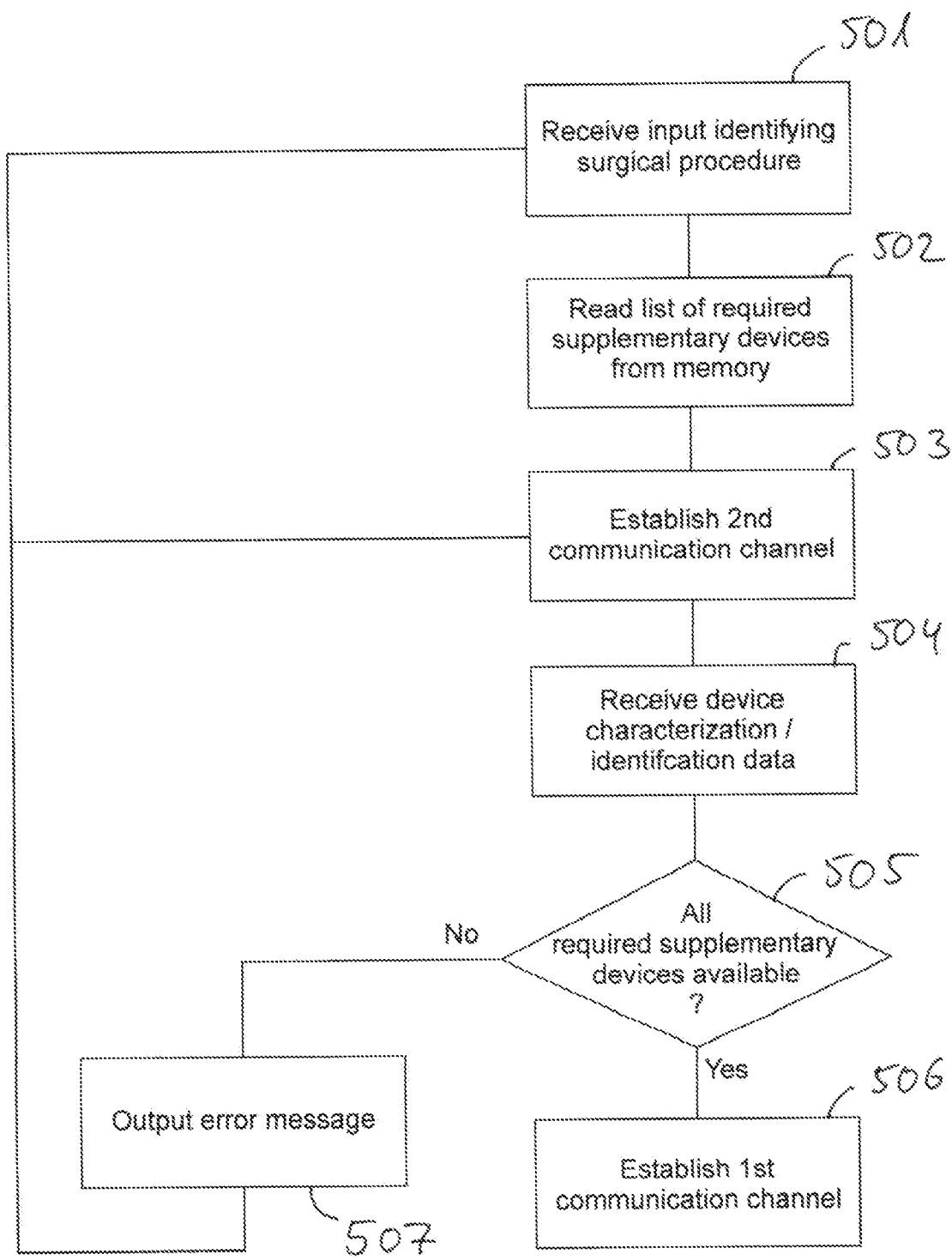
FIG. 5: a further method of operating a surgical device system.

FIG. 5 shows a further method of operating a surgical device system as described herein. In a first step 501, the electrosurgical generator may receive, through a user interface, input data identifying a surgical procedure to be performed. The step 501 may include reading a list of available procedures from a memory, which may be an internal memory of the electrosurgical generator, or an external memory. The list of available procedures may then be presented to a user through the user interface. The list of available procedures may be presented in several ways. In one example, a plurality of virtual selection buttons may be displayed on a graphic display, each virtual button assigned to one of the available procedures. The user may then select one of the procedures by activating the virtual button assigned to that procedure, e.g. by touching a touch display at a position where the virtual button is displayed. In a further example, the list of available procedures may be displayed as a list of text items naming and/or describing the respective procedure. The user may then scroll through the list of text items using virtual or physical scroll buttons, and select a procedure of interest through activation of a virtual or physical selection button.

In a second step 502, a list of supplementary devices required for the selected procedure is read from a memory. The memory may again be an internal memory of the electrosurgical generator, or an external memory. The list of required supplementary devices may be stored in a database.

In a third step 503, the electrosurgical generator established a second communication channel with one or more supplementary devices within the range of the second communication channel. Therefore, the electrosurgical generator sends an interrogation signal to be received by every supplementary device within the range of the interrogation signal. Any supplementary device receiving the interrogation signal may send a response signal to establish the second communication channel.

In step 504, the electrosurgical generator receives device characterization and/or identification data from the one or more supplementary devices through the second communication channel.

In step 505, the electrosurgical generator checks if all required supplementary devices are available, i.e. device characterization and/or identification data has been received from all required supplementary devices. If all required supplementary devices are available, the electrosurgical generator and the one or more supplementary devices establish a first communication channel for communicating operational data during performance of the selected procedure in step 506.

If one or more required supplementary devices have not provided device characterization and/or identification data through the second communication channel, the electrosurgical generator outputs an error message through a user interface in step 507. The error message may identify the type of supplementary device which is not available. The error message may prompt a user to select any appropriate measure. As one available measure, a user may perform any necessary actions to make the one or more missing supplementary devices available, e.g. by powering on a supplementary device which has accidentally been powered of, by bringing a supplementary device into the range of the second communication channel which had accidentally been placed outside of that range, or the like. The user may then select to resume the method with step 503. As a further available measure, the user may select to restart the method with step 501 to select a different procedure. As an even further available measure, a user may select to override the error message and continue with step 506.

In a modified method not shown in the drawings, the electrosurgical generator may first establish the second communication channel with any supplementary device within the range of the second communication channel, and receive device characterization and/or identification data from any supplementary device within the range of the second communication channel. The electrosurgical generator may then read from a memory a list of procedures that can be performed with the set of supplementary devices which have provided device characterization and/or identification data. The list may then be presented through the user interface so that a user may select one of the available procedures for execution. When reading the list of available procedures, the electrosurgical generator may apply an inclusive strategy, wherein all procedures are included in the list that can be performed with the set of supplementary devices available, or an exclusive strategy, wherein only those procedures are included in the list that require all of the supplementary devices available.

In the examples described above, it has been assumed that the electrosurgical generator acts as a master device of the surgical device system. In a modified surgical device system, a separate device, like a medical device controller, may act as a master device, and the electrosurgical generator acts as a further supplementary device of the surgical device system.

Figure 6:
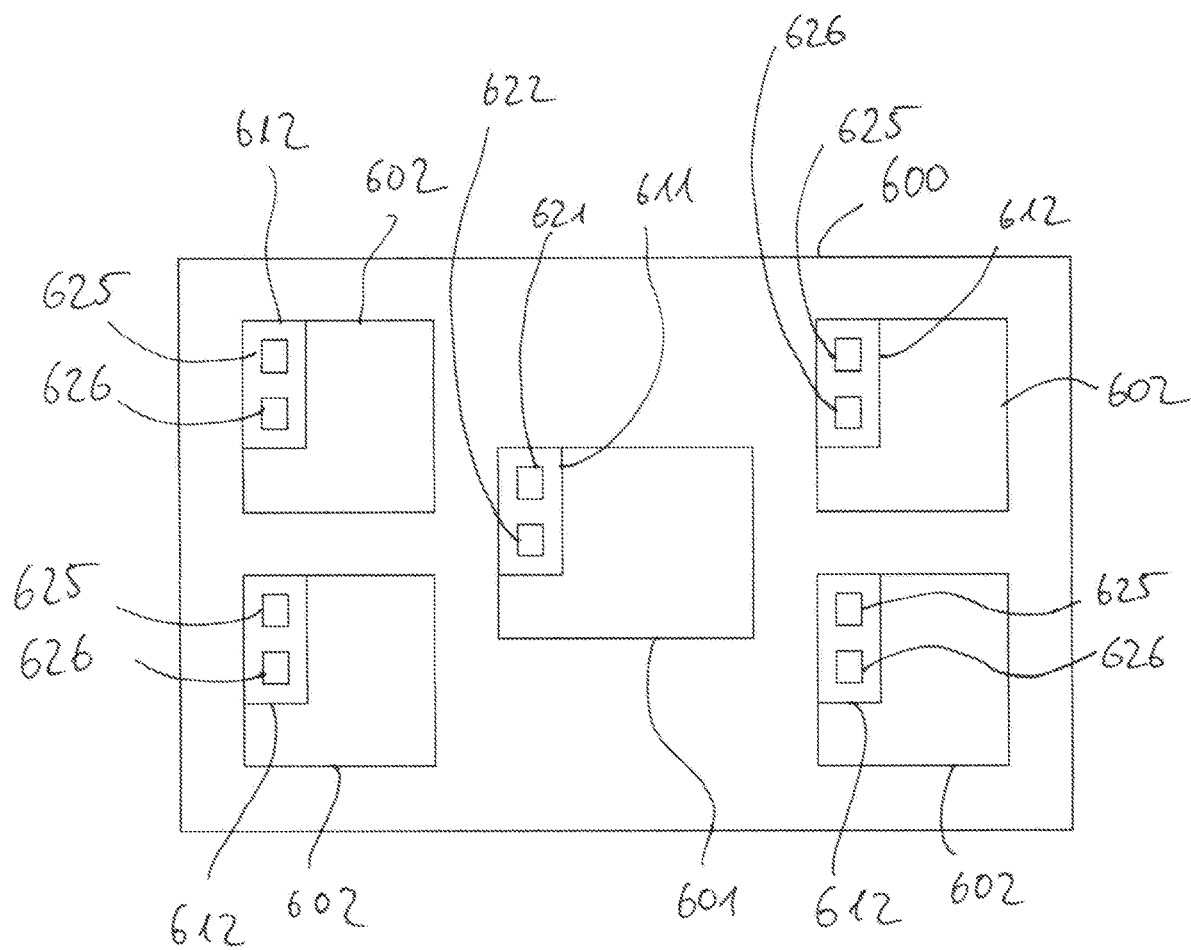
FIG. 6: a surgical device with a modular design.

In a further example shown in FIG. 6, a surgical device system may include a surgical device 600 provided in a modular design. The surgical device may include a master unit 601 and one or more slave units 602. While four slave units 602 are shown in FIG. 6. A higher or lower number of slave units 602 may be provide. The master unit 601 comprises a master wireless communication unit 611, and each of the slave units 602 may comprise a slave wireless communication unit 612. The master wireless communication unit 611 may comprise a first master communication feature 621 and a second master communication feature 622. The slave wireless communication unit 612 may comprise a first slave communication feature 625 and a second slave communication feature 626.

The master unit 601 may use the second master communication feature 622 to establish a second communication channel between the master 601 unit and the one or more slave units 602 through the second slave communication features. The second master communication feature 622 may be an RFID interrogator, an NFC interrogator, or the like. The second slave communication features 626 may be RFID transponders, NFC transponders, or the like.

For establishing the second communication channel, the master unit 601 may send an interrogation signal through the second master communication feature 622, and the one or more slave units 602 may send response signals through the second slave communication features 626.

After, or during, establishing the second communication channel, the master unit 601 and the one or more slave units 602 communicate, negotiate, and/or agree communication channel parameters for establishing a first communication channel using the first master communication feature 621 and the one or more first master communication features 625. The first master communication feature 621 and the first slave communication features 625 may be "WIFI" antennas, "Bluetooth" antennas, or the like. The master unit 601 and the one or more slave units 602 then establish the first communication channel to communicate operational data between the master unit 601 and the one or more slave units 602.

Through the modular design, the medical device 600 can be flexibly adjusted to the specific needs of a user. For example, the medical device 600 may include a standardized rack with a plurality of slots, one of which may be occupied by the master unit 601 and a power supply unit (not shown). The remaining slots may be available for slave units 602. Upon insertion of a slave unit 602 into an available slot, the slave unit 602 may automatically be connected to the power supply unit. Specific interfaces of the slave units 602 may be placed on front sides of the slave units 602, so they are accessible irrespective of how may slave units 602 are inserted in the rack. Slave units 602 may include electrosurgical generator units, microwave generator units, ultrasonic generator units, irrigation pump units, suction pump units, coolant pump units, and the like.

Figure 7:
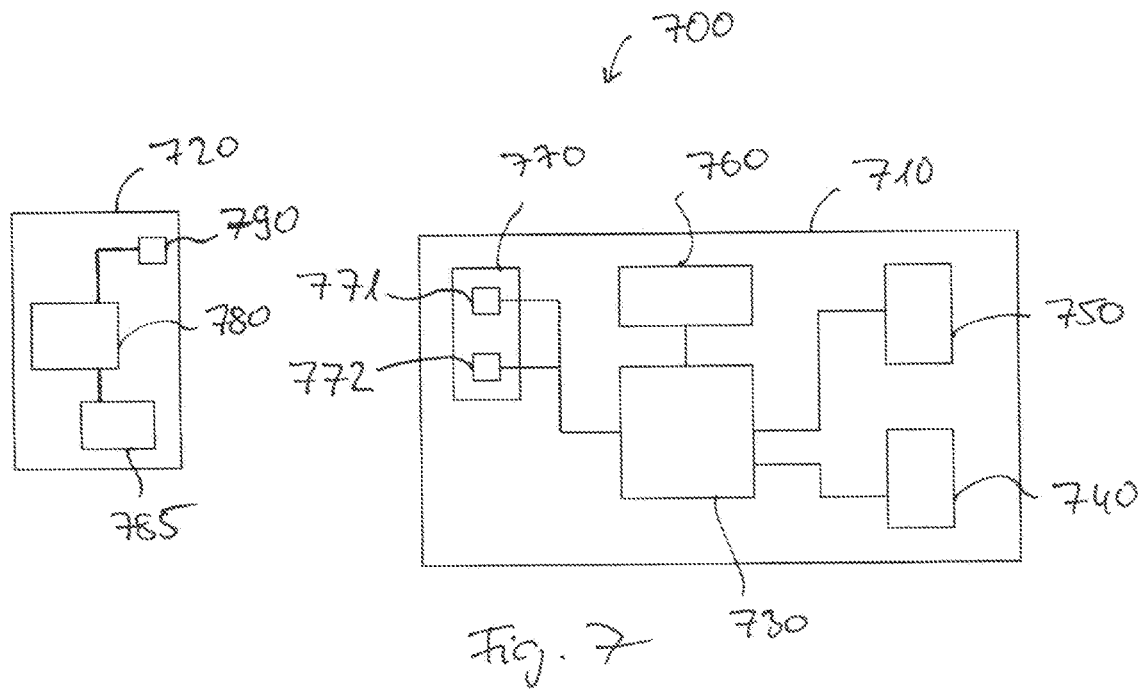
FIG. 7: a medical device system.

FIG. 7 shows a medical device system 700 according to a further embodiment of the present disclosure. The medical device system 700 comprises a medical device 710 and a wireless license tag 720.

The medical device may be similar to the electrosurgical generator 10 shown in FIG. 2, and comprise a control unit 730, a function unit 740, a user interface 750, a memory unit 760, and a wireless communication unit 770 with an RFID interrogator 771 and a WIFI antenna 772.

The medical device 710 is configured to provide a plurality of medical functionalities through the function unit 740. At least one of these functionalities is subject to a separate license from the manufacturer of the medical device 710. For enabling such functionalities, a license has to be registered with the medical device 710.

A user of the medical device 710 may purchase, or otherwise obtain, the wireless license tag 720 from the manufacturer of the medical device 720. The wireless license tag 720 comprises a controller 780, a memory element 785, and a wireless communication unit 790, which may be an RFID transponder. A license key is stored the memory element 785.

Figure 8:
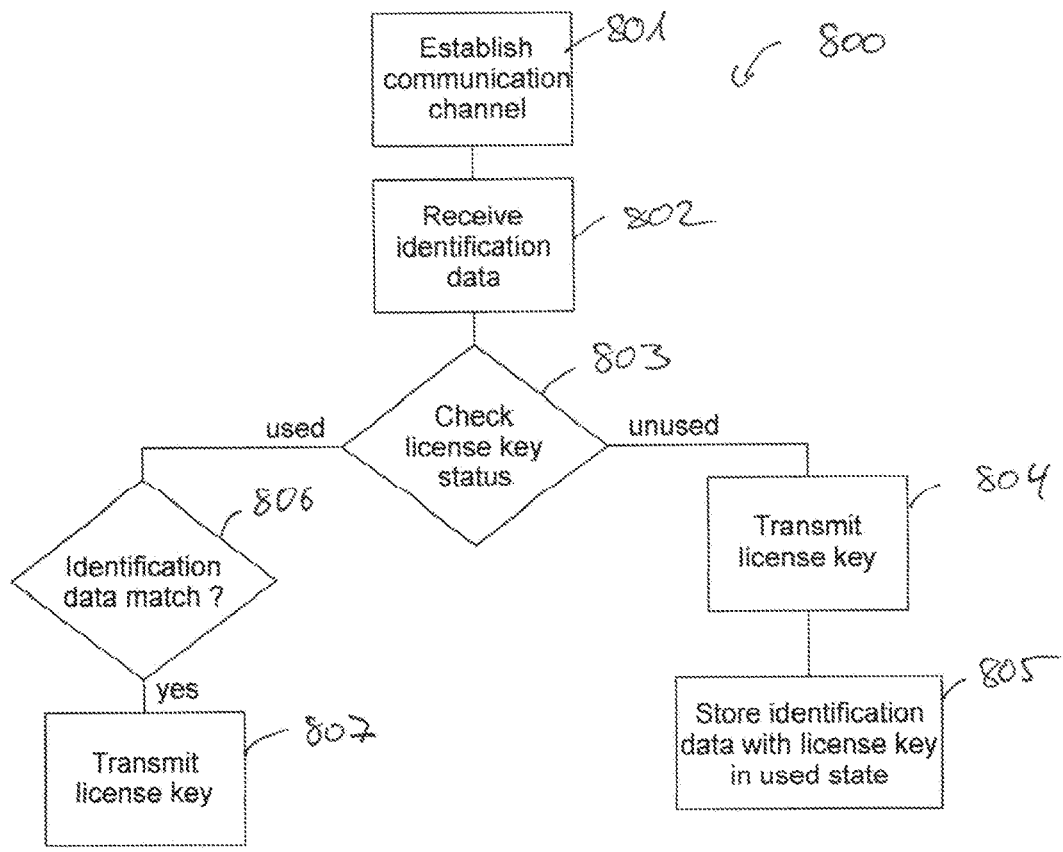
FIG. 8: a method of operating a medical device system.

A method 800 for registering the license with the medical device 710 is shown in FIG. 8.

In a first step 801, a wireless communication channel is established between the medical device 720 and the wireless license tag 720. Therefore, the controller 730 activates the RFID interrogator 771 to send an interrogation signal to be received by the RFID transponder 790 of the wireless license tag. The RFID transponder 790 sends a response signal to the RFID interrogator 771, establishing the wireless communication channel.

In a second step 802, the controller 730 activates the RFID interrogator 771 to send identification data identifying the medical device 710 through the wireless communication channel, which identification data is received by the RFID transponder 790 and forwarded to the controller 780 of the wireless license tag.

In a third step 803, the controller 780 of the wireless license tag 720 checks the status of the license key stored in the memory element 785. The license key may be stored in a first state representing an unused license key. The license key will usually be stored in the first state when the wireless license tag 720 is first provided by the manufacturer of the medical device 710. The unused state of the license key indicates that the license key may be registered with any compatible medical device, like the medical device 710.

If the license key is in the first state, the controller 780 of the wireless license tag 720 transmits the license key to the medical device 710 through the wireless communication channel in step 804.

To prevent use of the license key with other medical devices after it has been used with the medical device 710, the controller stores, in step 805, the license key on the memory element 785 in a second state, indicating that the license key has already been used with a certain medical device. For this purpose, the license key is stored on the memory element 785 together with the identification data of the medical device 710. The license key and the identification data can be stored as separate data element. The license key and the identification data can be combined into a single data element using a cryptographic function.

If, in step 803, the controller detects the license key being in the second state, it is checked in step 806 if the identification data received in step 802 matches the identification data stored with the license key. Therefore, an simple comparison or an inverse cryptographic function may applied.

If the identification data matches, the license key is again transferred to the medical device 710 in step 807. If the identification data does not match, the license key is not transmitted.

With the described method, multiple uses of the wireless license tag 720 with different medical devices can be prevented, while re-use of the wireless license tag with the same medical device is possible. This may e.g. be necessary if a license key registered with the medical device 710 gets lost, e.g. through a hardware reset or the like.

Figure 9:
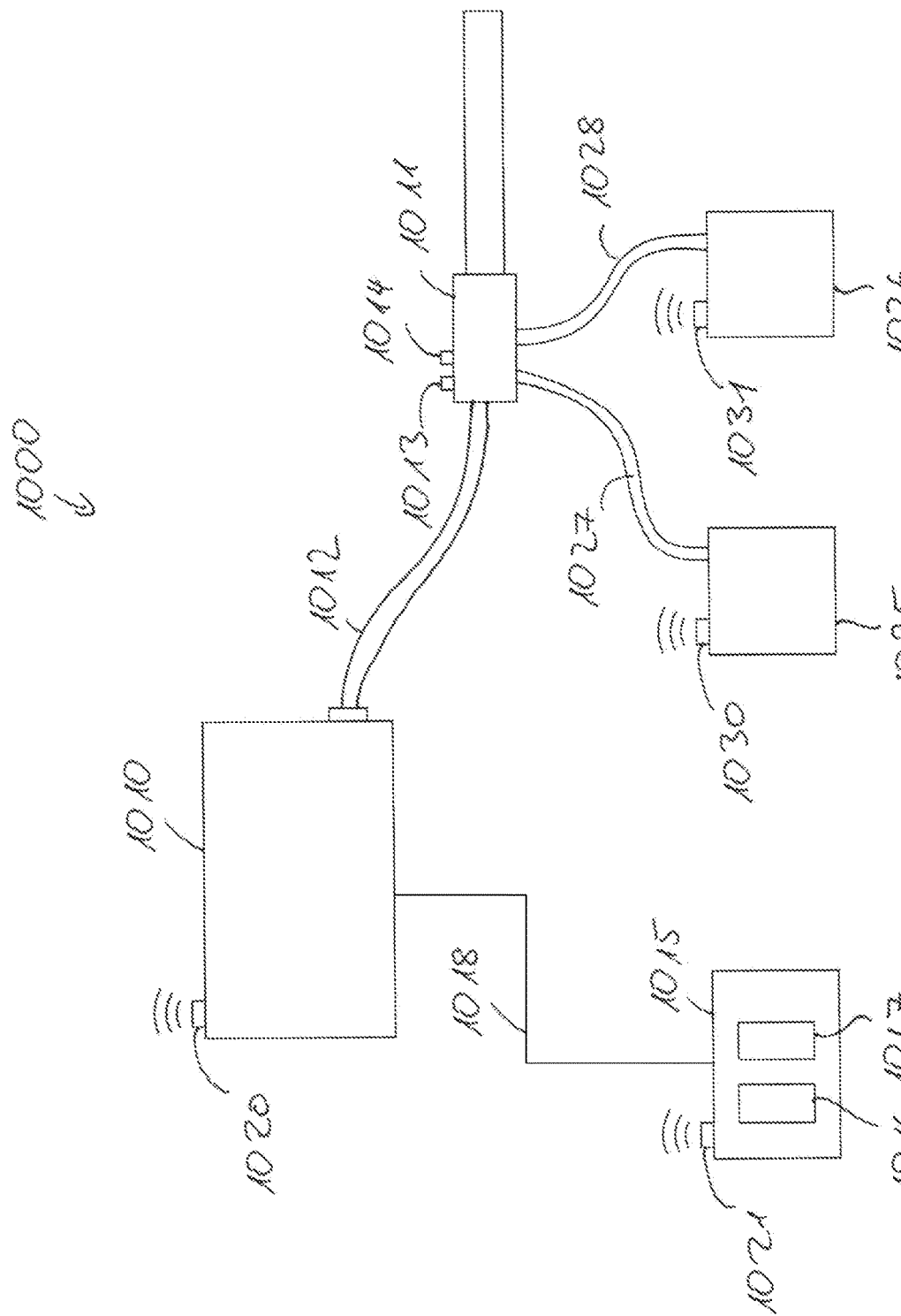
FIG. 9: a further surgical device system.

FIG. 9 shows a surgical device system 1000 according to a further embodiment of the present disclosure. The medical device system 1000 is similar to the medical device system 1 shown in FIG. 1, and corresponding elements are indicated by a reference number increased by 1000. In the present embodiment, the foot switch device 1015 is connected to the electrosurgical generator 1010 with a cable connection 1018.

During operation of the medical device system 1000, the electrosurgical generator 1010 and the foot switch device 1015 communicate operational data through a first, wirebound, communication channel established by the cable 1018, and the electrosurgical generator 1010 and the foot switch device 1015 further communicate supplementary data through a second, wireless communication channel established through the wireless communication units 1020, 1021.

In the present embodiment, the operational data may include essential operational data. Essential operational data may include operational data which is relevant for patient or procedural safety. Essential operational data may include operation data which must be communicated with low latency. Essential operational data may include activation and/or deactivation signals.

Supplementary data may include device characterization data or device identification data of the foot switch device 1015 for use in a method as described with relation to FIG. 5. Supplementary data may include operational date which need not be communicated with low latency.

In the medical device system 1000, a number of wires in the cable 1018 may be reduced when compared to the number of wires required in a cable for a conventional supplementary device. Alternatively, the volume of data communicated between the supplementary device 1015 and the electrosurgical generator 1010 may be increased, e.g. by providing a new supplementary device 1015 with enhanced functionalities, without the need to replace an existing cable 1018.

The invention claimed is:

1. A surgical device system, comprising:
at least one surgical instrument;
an electrosurgical generator for providing surgical energy to at least one surgical instrument;
at least one supplementary device for providing a supplementary function to at least one of the electrosurgical generator and/or the at least one surgical instrument;
a user interface configured to receive input data identifying a surgical procedure to be performed;
a memory configured to store a list of supplementary devices required for the surgical procedure to be performed;
the electrosurgical generator being configured to wirelessly communicate with the at least one supplementary device, wherein:

the electrosurgical generator and the at least one supplementary device are configured to establish a second communication channel for exchanging first communication channel parameters;
the second communication channel is configured to receive device identification data and/or device characterization data from supplementary devices within a range of the second communication channel;
the electrosurgical generator is configured to check if all supplementary devices required for the surgical procedure to be performed have provided device identification data or device characterization data in response to an interrogation signal, and
if the check is successful, establishing a first communication channel for exchanging operational data, the first communication channel being defined by the first communication channel parameters between the electrosurgical generator and the supplementary devices.

2. The surgical device system of claim 1, wherein a range of the second communication channel is shorter than a range of the first communication channel.

3. The surgical device system of claim 1, wherein a bandwidth of the second communication channel is lower than a bandwidth of the first communication channel.

4. The surgical device system of claim 1, wherein the second communication channel is a Near Field Communication "NFC" channel.

5. The surgical device system of claim 1, wherein the second communication channel is a Radio Frequency Identification "RFID" channel.

6. The surgical device system of claim 1, wherein the first communication channel is an IEEE 802.11 "WiFi" communication channel.

7. The surgical device system of claim 1, wherein the first communication channel is a "Bluetooth" communication channel, an IEEE802.15.4 communication channel, or a "ZigBee" communication channel.

8. The surgical device system of claim 1, wherein the at least one supplementary device is configured to transmit device characterization data and/or device identification data through the second communication channel.

9. The surgical device system according to claim 1, wherein the at least one supplementary device includes at least one of a foot switch, a smoke evacuator, an irrigation pump, a suction pump, and a coolant pump.

10. The surgical device system according to claim 1, wherein the operational data include at least one of an activation signal, a deactivation signal, a target flow rate, a current flow rate, a target pressure, a current pressure, a target temperature, a current temperature, a battery status, a connection quality, and a heartbeat signal.

11. The surgical device system according to claim 1, wherein the electrosurgical generator is configured to receive, through a network connection, software update data for one or more of the supplementary devices, and to communicate such software update data to the one or more supplementary devices.

12. A surgical device system, comprising:
at least one surgical instrument;
a electrosurgical generator for providing surgical energy to at least one surgical instrument;
at least one supplementary device for providing a supplementary function to at least one of the electrosurgical generator and/or the at least one surgical instrument;
a user interface configured to receive input data identifying a surgical procedure to be performed; and a memory configured to store a list of supplementary devices required for the surgical procedure to be performed;

the electrosurgical generator being configured to communicate with the at least one supplementary device, wherein:

the electrosurgical generator and the at least one supplementary device are configured to establish a second, wireless communication channel for exchanging supplementary data;

the second, wireless communication channel is configured to receive device identification data and/or device characterization data from supplementary devices within a range of the second, wireless communication channel;

the electrosurgical generator is configured to check if all supplementary devices required for the surgical procedure to be performed have provided device identification data or device characterization data in response to an interrogation signal, and if the check is successful, establishing a first, wire-bound communication channel for exchanging operational data between the electrosurgical generator and the supplementary devices.

13. A surgical generator of a surgical device system according claim 1.

14. A supplementary device of a surgical device system according to claim 1.

15. The surgical device system according to claim 1, wherein:

if the check has not been successful, outputting, through the user interface, an error message identifying missing supplementary devices required for the surgical procedure to be performed.

16. A medical device, comprising a control unit and a function unit, wherein the medical device is configured to provide a plurality of medical functionalities through the function unit, at least one of the plurality of medical functionalities being subject to a license, wherein:

the medical device further comprises a wireless communication unit configured to establish a wireless communication channel with a wireless license tag, and to obtain a license key for at least one of the plurality of medical functionalities from the wireless license tag;

the wireless license tag is configured to store the license key in a first state and a second state, the first state representing an unused license key, and the second state representing a used license key;

the wireless license tag is configured to change a state of the stored license key from the first state to the second state after communication of the license key to the medical device;

the wireless license tag is configured to receive, after establishing the wireless communication channel with the medical device, medical device identification data through the wireless communication channel, and to store the medical device identification data together with the license key in the second state; and the wireless license tag is configured to, when the license key is stored in the second state, communicate the license key to the medical device only if the medical device identification data received from the medical device matches the medical device identification data stored with the license key.

17. The medical device of claim 16, wherein the medical device is configured to communicate, after establishing the wireless communication channel with the wireless license tag, medical device identification data through the wireless communication channel.

18. A wireless license tag, the wireless license tag being configured to establish a wireless communication channel with a medical device, and to communicate a license key to the medical device, the license key being stored on a memory element of the wireless license tag, wherein:

the wireless license tag is configured to store the license key in a first state and a second state, the first state representing an unused license key, and the second state representing a used license key;

the wireless license tag is configured to change the state of the stored license key from the first state to the second state after communication of the license key to the medical device;

the wireless license tag is configured to receive, after establishing the wireless communication channel with the medical device, medical device identification data through the wireless communication channel, and to store the medical device identification data together with the license key in the second state; and the wireless license tag is configured to, when the license key is stored in the second state, communicate the license key to the medical device only if the medical device identification data received from the medical device matches the medical device identification data stored with the license key.

* * * * *